(12) United States Patent
Khalaf et al.

(10) Patent No.: US 9,869,604 B2
(45) Date of Patent: Jan. 16, 2018

(54) APPARATUS AND METHOD FOR DETECTING LEAKAGE FROM A COMPOSITION-CONTAINING POUCH

(71) Applicant: The Procter & Gamble Company, Cincinnati, OH (US)

(72) Inventors: Suzanne Khalaf, Brussels (BE); Stefan Meskens, Londerzeel (BE); Kerry Brian Johnson, Jackson, TN (US); Leon Byrd, Jr., Belleville, IL (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/270,071

(22) Filed: Sep. 20, 2016

(65) Prior Publication Data

US 2017/0030797 A1    Feb. 2, 2017

Related U.S. Application Data

(63) Continuation of application No. 13/406,254, filed on Feb. 27, 2012, now Pat. No. 9,470,638.

(51) Int. Cl.
*G01N 21/01* (2006.01)
*G01M 3/22* (2006.01)
(Continued)

(52) U.S. Cl.
CPC .............. *G01M 3/227* (2013.01); *G01M 3/38* (2013.01); *G01N 21/9081* (2013.01); *G01N 21/95* (2013.01); *G01N 21/894* (2013.01)

(58) Field of Classification Search
CPC ......... G01N 33/57484; G01N 2333/08; G01N 33/57434; G01N 33/6803; G01N 2500/10;
(Continued)

(56) References Cited

U.S. PATENT DOCUMENTS 3,942,900 A    3/1976 Garris
5,281,826 A    1/1994 Ivancic et al.
(Continued)

FOREIGN PATENT DOCUMENTS

| CN | 1 910 433 A | 2/2007 |
|---|---|---|
| JP | 2004 028604 A | 1/2004 |
| WO | WO 2007/134632 A1 | 11/2007 |

OTHER PUBLICATIONS

PCT Search report dated Nov. 25, 2013; 10 Pages.
(Continued)

*Primary Examiner* — Michael P Stafira
(74) *Attorney, Agent, or Firm* — Gregory S. Darley-Emerson; Leonard W Lewis; Steven W Miller

(57) ABSTRACT

An apparatus and a method for detecting leakage from a composition-containing pouch during the high-speed manufacturing process. The apparatus comprises: a platen comprising a pouch cavity and a plurality of platen edges adjacent to the cavity; an image capturing unit; an image processing unit; and ultraviolet-light emitting source. The composition itself comprises a fluorescent whitening compound. The ultra-violet emitting light source is arranged to illuminate the cavity and plurality of platen edges. The image capturing unit is arranged to capture an image of the illuminated cavity and plurality of platen edges. The image capturing unit is communicably attached to the image processing unit.

22 Claims, 6 Drawing Sheets

(51) Int. Cl.
*G01M 3/38* (2006.01)
*G01N 21/95* (2006.01)
*G01N 21/90* (2006.01)
*G01N 21/894* (2006.01)

(58) Field of Classification Search
CPC ......... G01N 2333/485; G01N 2500/00; G01N 2800/52; G01N 2333/52; G01N 2800/2821; G01N 33/5008; G01N 33/6845; G01N 33/6893
See application file for complete search history.

(56) References Cited

U.S. PATENT DOCUMENTS

| | | | |
|---|---|---|---|
| 5,363,968 A | 11/1994 | Soloman et al. | |
| 5,568,715 A | 1/1996 | Ebel et al. | |
| 5,515,159 A | 5/1996 | Sites et al. | |
| 6,154,274 A | 11/2000 | Davis et al. | |
| 6,351,984 B1 | 3/2002 | Srinivasan | |
| 7,142,707 B2 * | 11/2006 | Abdollahi | G01N 21/95 382/108 |
| 7,434,986 B2 | 10/2008 | Ignatowitz | |
| 8,697,624 B2 * | 4/2014 | Denome | B65D 65/46 206/524.7 |
| 8,853,142 B2 | 10/2014 | Corominas et al. | |
| 9,233,768 B2 | 1/2016 | Meskens et al. | |
| 9,470,638 B2 * | 10/2016 | Khalaf | G01M 3/227 |
| 2005/0050451 A1 * | 3/2005 | Abdollahi | G01N 21/95 715/210 |
| 2007/0296963 A1 | 12/2007 | Parker et al. | |
| 2010/0115887 A1 | 5/2010 | Schroeder et al. | |
| 2010/0276344 A1 | 11/2010 | Yamada et al. | |
| 2011/0188784 A1 | 8/2011 | Denome | |
| 2011/0257063 A1 * | 10/2011 | Lant | C11D 3/0047 510/305 |
| 2013/0222602 A1 | 8/2013 | Khalaf et al. | |
| 2014/0200701 A1 | 7/2014 | Kent et al. | |

OTHER PUBLICATIONS

Forcinio, Hallie, Packaging Innovations Interphex serves as a showcase for new materials and machines; Packaging Forum, Aug. 2003, pp. 18-26.

* cited by examiner

APPARATUS AND METHOD FOR DETECTING LEAKAGE FROM A COMPOSITION-CONTAINING POUCH

FIELD OF THE INVENTION

This disclosure relates to a machine vision method for detecting leakage from a composition-containing pouch during the manufacturing process and an apparatus used therefore.

BACKGROUND OF THE INVENTION

Consumer products are manufactured on high-speed production lines. A production line typically includes a series of steps or stations at which different portions of the consumer product are made and/or modified. These steps are often accomplished at the highest possible speed, so as to achieve a high output and low production costs. Yet it is still desirable to maintain the required quality standards for the consumer product. As such, high-speed production lines typically include a means of inspecting the completed consumer product(s).

Manual or digital inspection of every single product at the end of a high-speed production line may be inefficient for a number of reasons. First, it is time consuming to inspect each and every consumer product that comes off of a high-speed production line. Indeed, it oftentimes is simply impractical. One solution to this problem is to manually or digitally inspect a sampling of the consumer product. However, use of this approach ultimately may mean that that some faulty consumer products escape the inspection process and/or faulty products are not identified until it is too late to correct outages along the production line. This can result in whole batches of faulty consumer products, which may not be marketable "as is."

Consumer made along high-speed production lines include pouches that are used to package household care compositions such as laundry or dish detergent. The current pouches on the market include single compartment pouches as well as multi-compartment pouches, which are collectively referred to herein as "unit dose pouches." The compartments are manufactured along high-speed production lines using platens comprising a series of mold cavities into which water-soluble film is drawn and is deformed such that it takes the cavity's shape. The resulting compartments may then be sealed to form a single-compartment pouch or at least a portion of a multi-compartment pouch. In this way, multiple unit dose pouches are made simultaneously. If at least one of those unit dose pouches is defective, the composition may leak, causing contamination of the production line and/or other unit dose pouches.

SUMMARY OF THE INVENTION

There remains a need for an efficient, fast and thorough method and apparatus for inspecting unit dose pouches for quality assurance as they are being made along a high-speed production line. The present disclosure addresses the aforementioned need by providing a converter-integrated machine apparatus and a method for monitoring the quality of unit dose pouches.

A new apparatus for detecting leakage from a composition-containing pouch during the high-speed manufacturing process is described herein. The apparatus comprises: a platen comprising a pouch cavity and a plurality of platen edges adjacent to the cavity; an imaging unit; an image processing unit; and an actinic radiation emitting source. The actinic radiation emitting source may be an ultra violet light. The actinic radiation-emitting source is arranged to expose at least one of the plurality of platen edges with actinic radiation. The imaging unit is arranged to obtain an image of the at least one of the plurality of platen edges exposed to the actinic radiation. The imaging unit is communicably attached to the image processing unit.

A new method for detecting leakage from a composition-containing pouch is described herein. The method may be performed along a production line one or more times. The composition-containing pouch is located in the cavity of a platen disposed in a pouch converting line. The composition comprises a photoactive compound that is responsive to actinic radiation. The platen has a plurality of platen edges adjacent to the cavity. The method comprises the following steps. At least one of the plurality of platen edges is exposed to the actinic radiation-emitting source. An image of the at least one of the plurality of platen edges exposed to actinic radiation is obtained. Actinic radiation emitted from the photoactive compound, if present on the at least one of the plurality of platen edges, is detected. If actinic radiation emission is detected, a fail message is sent to a controller such as a programmable converter ("PLC") or programmable automation controller ("PAC"). Optionally, the controller may then direct the leaky pouch and/or pouch(es) located in an adjacent cavity or cavities to be ejected from the converting line.

BRIEF DESCRIPTION OF THE DRAWINGS

The present disclosure may be more readily understood with reference to the appended drawing figures where.

DETAILED DESCRIPTION OF THE INVENTION

Figure 1:
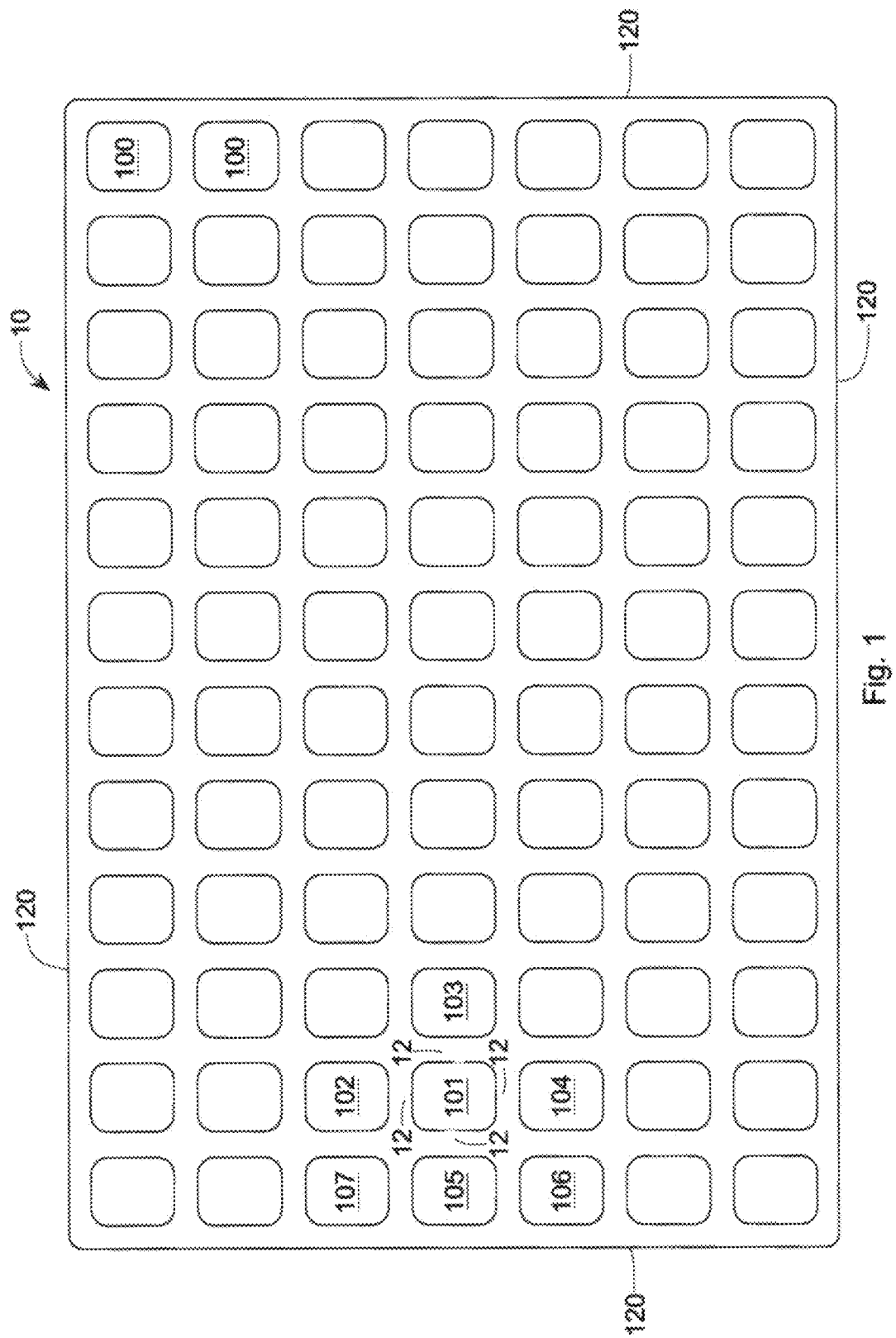
FIG. 1 is a plan view of a section of a plurality of molds located on a platen.

"Comprising" as used herein means that various components, ingredients or steps can that be conjointly employed in practicing the present disclosure. Accordingly, the term "comprising" encompasses the more restrictive terms "consisting essentially of" and "consisting of". The present compositions can comprise, consist essentially of, or consist of any of the required and optional elements disclosed herein.

Manufacturing Process

Unit dose pouches are made using suitable equipment and methods. For example, unit dose pouches are made using vertical form filling, horizontal form filling, and/or rotary drum filling techniques commonly known in the art. Such processes may be either continuous or intermittent. Examples of continuous in-line processes of manufacturing water-soluble containers are set forth in U.S. Pat. No. 7,125,828, U.S. 2009/0199877A1, EP 2380965, EP 2380966, U.S. Pat. No. 7,127,874 and US2007/0241022 (all to Procter & Gamble Company, Ohio, USA). Examples of non-continuous in-line processes of manufacturing water-soluble containers are set forth in U.S. Pat. No. 7,797,912 (to Reckitt Benckiser, Berkshire, GB). Each of these processes may utilize a platen comprising a plurality of mold cavities.

Generally, the process may comprise the following steps. A film is heated and/or wetted and fed onto the surface of the platen. Once on the surface of the platen, the film can be held in position by any means. For example, the film can be held in position through the application of vacuum on the film, thus pulling the film in a fixed position on the surface. The vacuum may be applied along the edges of the film and/or on the surface area between the mold cavities. The platen surface may have at least some holes connected to a unit which can provide a vacuum as is known in the art.

Any film that is suitable for making a unit dose pouch is used. Non-limiting examples of water-soluble films that are used include those comprising polyvinyl alcohol as described in: U.S. 2011/0204087A1 and U.S. 2011/0188784A1 (each to Procter & Gamble Company, Ohio, USA). Further non-limiting examples include commercially available films including: M8630 and M8900 supplied by MonoSol (Gary, Ind., USA) and/or films known under trade reference Solublon® of films supplied by Aicello (North Vancouver, BC, Canada) or Poval film supplied by Kuraray (Houston, Tex., USA).

Once open pockets of film are formed into the mold cavities, they may be filled with composition and sealed by any known method, including those described in the patent publications listed above. The sealing step typically is accomplished by sealing a second water-soluble film to the open top of the pocket. In some embodiments, the second water-soluble film may itself form a portion of one or more composition containing pockets. Non-limiting filling and sealing means are described in U.S. Pat. No. 6,995,126, U.S. Pat. No. 7,125,828, U.S. 2009/0199877A1, EP 2380965, EP 2380966, U.S. Pat. No. 7,127,874 and US2007/0241022 (all to Procter & Gamble Company, Ohio, USA).

Composition

The unit dose pouches may contain any composition that is suitable for an intended us. Non-limiting examples of useful compositions include light duty and heavy duty liquid detergent compositions, hard surface cleaning compositions, detergent gels commonly used for laundry, and bleach and laundry additives, shampoos, body washes, and other personal care compositions. The compositions may take the form of a liquid, gel, solid or a powder. Liquid and gel compositions may comprise a solid. Solids may include powder or agglomerates, such as micro-capsules, beads, noodles or one or more pearlized balls or mixtures thereof.

Compositions useful in the present disclosure comprise a photosensitive compound. When exposed to an actinic radiation source, the photosensitive compound emits actinic radiation. Photosensitive compounds of use in the present invention include fluorescent dyes, ultraviolet dyes, near infrared dyes and infrared dyes, such as those that are used as optical brighteners, i.e., compounds that tint laundry articles. Optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous compounds. Examples of such brighteners are disclosed in "The Production and Application of Fluorescent Brightening Agents", M. Zahradnik, Published by John Wiley & Sons, New York (1982). Non-limiting examples of optical brighteners which are useful in the present compositions are those identified in U.S. Pat. No. 4,790,856 and U.S. Pat. No. 3,646,015.

Non-limiting examples of stillbene derivatives of use include the following. Colour Index ("C.I.") fluorescent brightener 260 in predominantly the alpha-crystalline form and having the following structure:

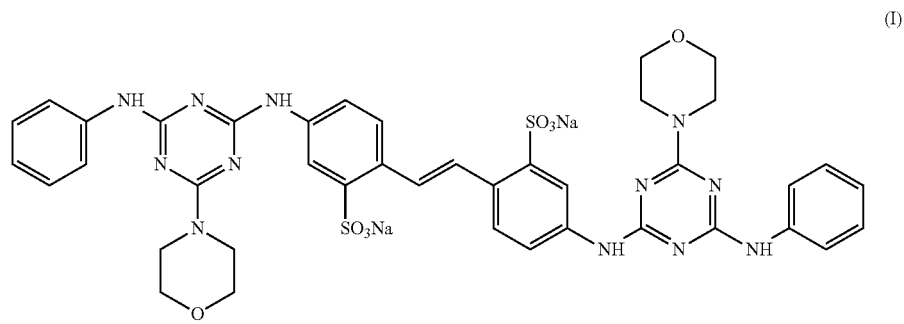

(I)

"Predominantly in alpha-crystalline form," means that typically at least 50 wt %, at least 75 wt %, at least 90 wt %, at least 99 wt %, or even substantially all, of the C.I. fluorescent brightener 260 is in alpha-crystalline form. This brightener is typically in micronized particulate form, having a weight average primary particle size of from three to thirty micrometers, from three micrometers to twenty micrometers, or from three to ten micrometers. The composition may comprise C.I. fluorescent brightener 260 in beta-crystalline form, and the weight ratio of: (i) C.I. fluorescent brightener 260 in alpha-crystalline form, to (ii) C.I. fluorescent brightener 260 in beta-crystalline form may be at least 0.1, or at least 0.6. BE680847 relates to a process for making C.I fluorescent brightener 260 in alpha-crystalline form.

A further stilbene derivative of use has the structure below:

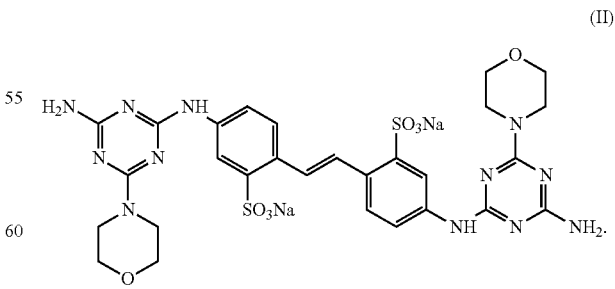

(II)

Suitable fluorescent brightener levels include lower levels of from about 0.01, from about 0.05, from about 0.1 or even from about 0.2 wt % to upper levels of 0.5 or even 0.75 wt %.

Further stilbene derivatives of use include 2,2'-(1,2-ethenediyl)bis[5-[[4,6-bis(phenylamino)-1,3,5-triazin-2-yl]amino]benzenesulfonic acid, and 4,4'-BIS (2-DISULFONIC ACID STYRYL) BIPHENYL, which is also known as C.I. Fluorescent Brightener 351. One of skill in the art may determine the minimum and maximum amount of actinic radiation emitting compound to use based upon the desired level of actinic radiation emission. Often this consideration is balanced against the cost and/or usefulness of the compound in the composition as well as the sensitivity of the image unit utilized to detect the actinic radiation emitting compound.

In one example, useful concentrations of fluorescent whitening compound are from about 50 parts per million ("ppm") to about 2500 ppm, from about 100 ppm to about 2000 ppm, and from about 200 ppm to about 1500 ppm.

Platen

Typical unit dose manufacturing lines utilize a surface containing the mold cavity for each compartment that forms the unit dose pouch. Often, the surface is removably connected to a moving, rotating belt, for example a conveyer belt or platen conveyer belt. The movement of the belt may be continuous or intermittent. The surface can be removed as needed and replaced with another surface having other dimensions or comprising moulds of a different shape or dimension. This allows the equipment to be cleaned easily and to be used for the production of different types of unit dose pouches. Any useful surface may be used.

Referring now to FIG. 1, one embodiment of a platen 10 of use is shown. In FIG. 1, a plurality of mold cavities 100 are present in a 2-D array on the surface of the platen 10. In this embodiment there are twelve mold cavities in the machine direction of the platen and seven mold cavities in the cross-machine direction. Each cavity may be defined by a Row, "R," in the machine direction and a Lane, "L," in the cross machine direction. It follows that since there is a plurality of mold cavities on the surface of the platen that each cavity has at least three neighboring cavities except for those mold cavities directly adjacent to the four edges of the platen itself 120. For example cavity 101 in FIG. 1 has four neighboring cavities, 102, 103, 104 and 105, whereas cavity 105, which is on the edge of the platen itself 120, has only three neighboring cavities 101, 106 and 107. Between the cavity 101 and each of its four neighboring cavities are platen edges 12 adjacent to the cavity.

Figure 2:
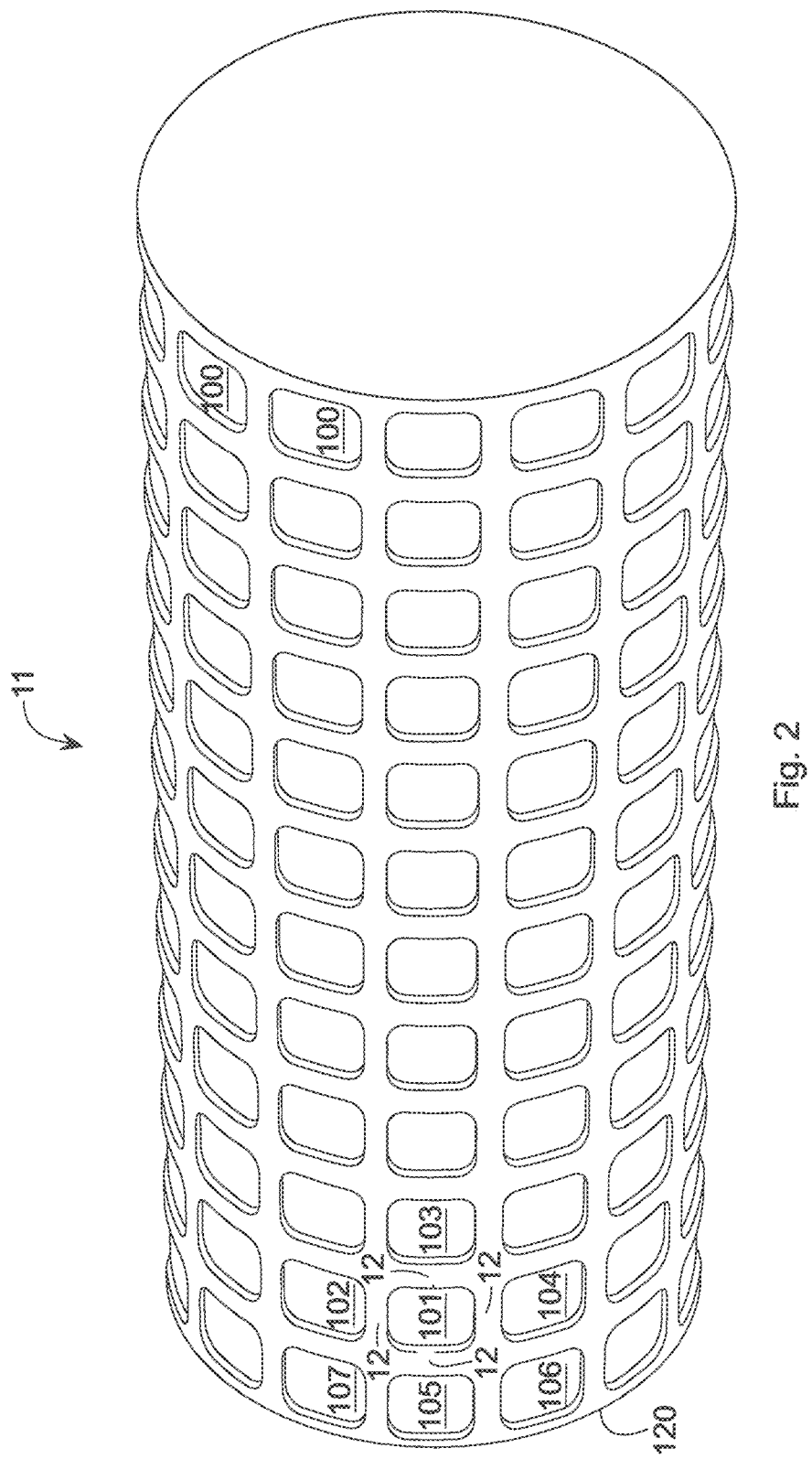
FIG. 2 is a plan view of a section of a plurality of molds located on a circular drum.

FIG. 2 depicts another useful embodiment of a platen 10. The mold cavities 100 are located on the curved surface of a drum 11. Like the platen described above, there are a plurality of mold cavities on the surface of the drum, such that each cavity has at least two neighboring cavities.

Unit Dose Pouches

Single or multi-compartment pouches may be made utilizing the mold cavities such as those described above. Non-limiting examples of single compartment pouches and methods of making them are those that are presently on the market under the names Tide Pods, All Mighty Pacs, Purex Ultra Packs, Persil, OMO Pods, Tesco Capsules, Arm & Hammer Crystal Power Pacs. Non-limiting examples of multi-compartment pouches and methods of making unit dose pouches are described in U.S. 2010/0192986A1, U.S. Pat. No. 6,995,126, U.S. Pat. No. 7,125,828, U.S. Pat. No. 7,127,874, U.S. Pat. No. 7,964,549, U.S. 2009/0199877A1, U.S. Pat. No. 6,881,713, U.S. Pat. No. 7,013,623, U.S. Pat. No. 7,528,099, and U.S. Pat. No. 6,727,215 (each to the Procter & Gamble Company, Ohio, USA). Tide Pods and Ariel Pods are examples of multi-compartment pouches that are currently on the market.

Actinic Radiation-Emitting Source

Any suitable actinic radiation emitting source may be utilized to cause the photoactive compound(s) in the composition to emit actinic radiation. Non-limiting examples of suitable actinic radiation emitting sources include: an ultraviolet light; a white light; a near infra red light; an infra red light; and combinations thereof.

Imaging Unit

The inspection of the unit dose pouch and/or the at least one of the platen edges adjacent to the cavity in which the unit dose pouch is located can be accomplished using any suitable camera or other optical picture-capturing device. Non-limiting examples of cameras of use include a line scan camera such as the In-Sight 5604 Camera from Cognex (Natick, Mass., USA), one of the PC line of cameras from Teledyne Dalsa (Billerica, Mass., USA), the Elixa UC8 or one of the Aviiva line of cameras from e2v (Tarrytown, N.Y., USA), or the spL8192-39k or spL4096-70 k from Basler AG (Ahrensburg, Germany).

Image Processing Unit

The image processing unit may be a stand-alone unit or it may be an integral part of the camera. One non-limiting example of an integrated camera and image processing unit is the In-Sight 5604 Camera from Cognex (Natick, Mass., USA). The image processing unit inspects the image captured by the camera to look for actinic radiation being emitted from at least one of the platen edges surrounding the composition-containing pouch. If actinic radiation is detected on a platen edge, then the image processing unit sends a fail message to the controller.

In one embodiment, the image processing unit integrates the captured image and executes a programmed process to analyze the image. Based upon the results of the image analysis, a pass or fail decision is communicated to the controller.

Controller

A programmable controller is utilized. A suitable controller is selected from a programmable automation controller or a programmable logic controller. A useful programmable automation controller may be selected from the Control Logic family of programmable automatic controllers from Rockwell Automation (Anaheim, Calif., USA).

EXAMPLES

Figure 3:
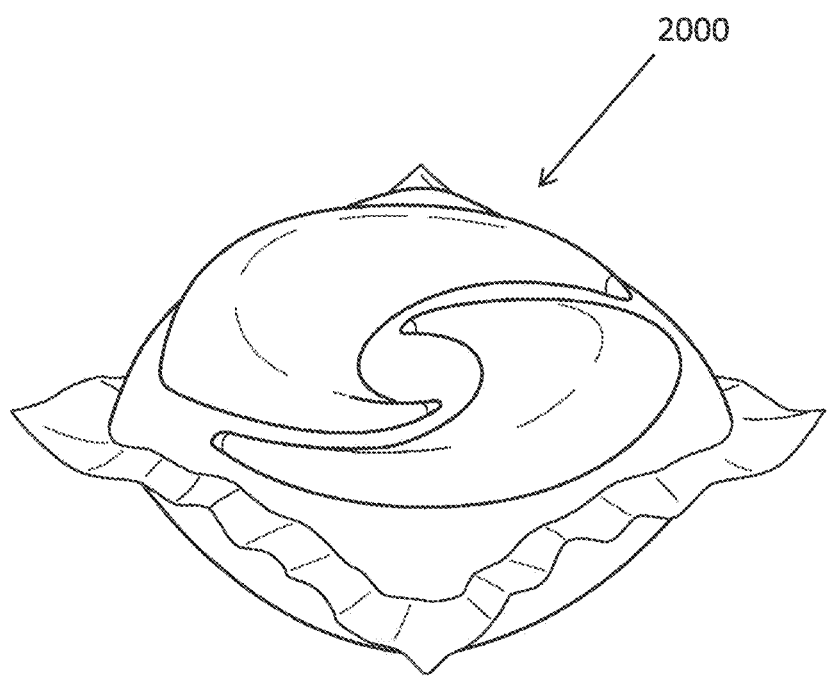
FIG. 3 is a three compartment unit dose pouch.

A unit dose pouch 2000 comprising three compartments as shown in FIG. 3 is present in a cavity of a platen after being sealed. The compartments each contain 50 parts per million of C.I. Fluorescent Brightener 351. A vision apparatus according to the present disclosure is mounted in-line with the unit dose pouch production line after the stage at which the three compartments are sealed to each other.

Figure 4:
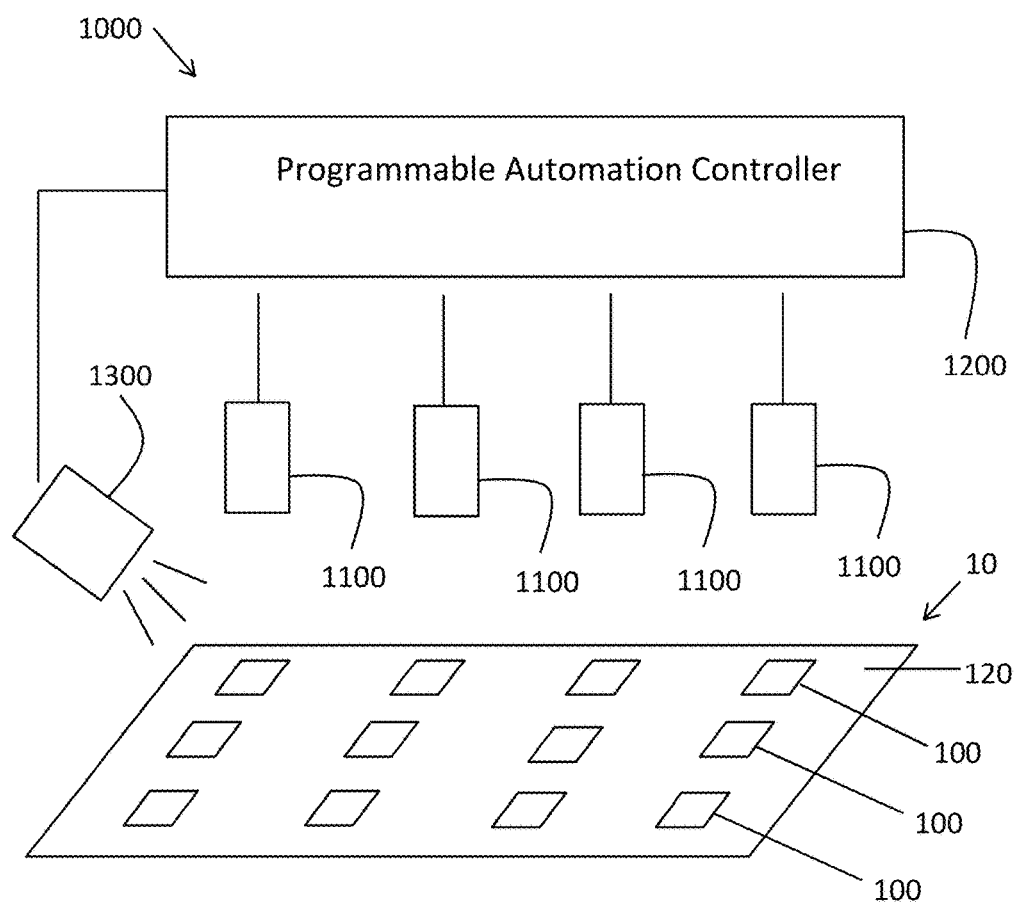
FIG. 4 is a block diagram of an exemplary vision apparatus.

FIG. 4 shows a block diagram of a vision apparatus 1000 according to the present disclosure. A series of Cognex In-Sight 5604 line scan vision cameras 1100 are positioned above the platen 10 and span the platen in the cross machine direction. The camera utilizes a CCD chip (imager), which consists of a single row of pixels. The single row of pixels is captured repeatedly in real time synchronized with the motion of the speed of the converter. In this way, an image of each cavity in the platen and the edges adjacent to the cavity is captured. The camera software assembles the individual rows of pixels into a single area image.

An ultraviolet light-emitting diode line light ("UV light") 1300 is mounted and directed at the pouch platen 10 to line up with the camera focal center lines for lighting the cavities to be inspected by the cameras. When the converter motion begins, the UV light 1300 is powered on by the programmable automation controller ("PAC") 1200. When powered on, the UV light 1300 emits actinic radiation that excites the C.I. Fluorescent Brightener 351 located in the pouch and, if present, on the platen edges surrounding the pouch. The cameras are triggered simultaneously by an output from the line's PAC that communicates with the cameras via an Ethernet switch. After an image of the pouches and platen edges surrounding the pouches is captured and integrated into a single bitmap, the cameras execute the programmed process to analyze the image. At the same time that this image is analyzed, another trigger input from the PAC signals the cameras to begin capturing data for the next-in-line pouches and the platen edges surrounding those pouches.

A pass/fail decision is evaluated for each pouch location on the converter platen. The pass/fail decision is communicated to the PAC via an Ethernet switch. Each row and lane is determined to pass or fail if it contains a leaker.

Figure 5:
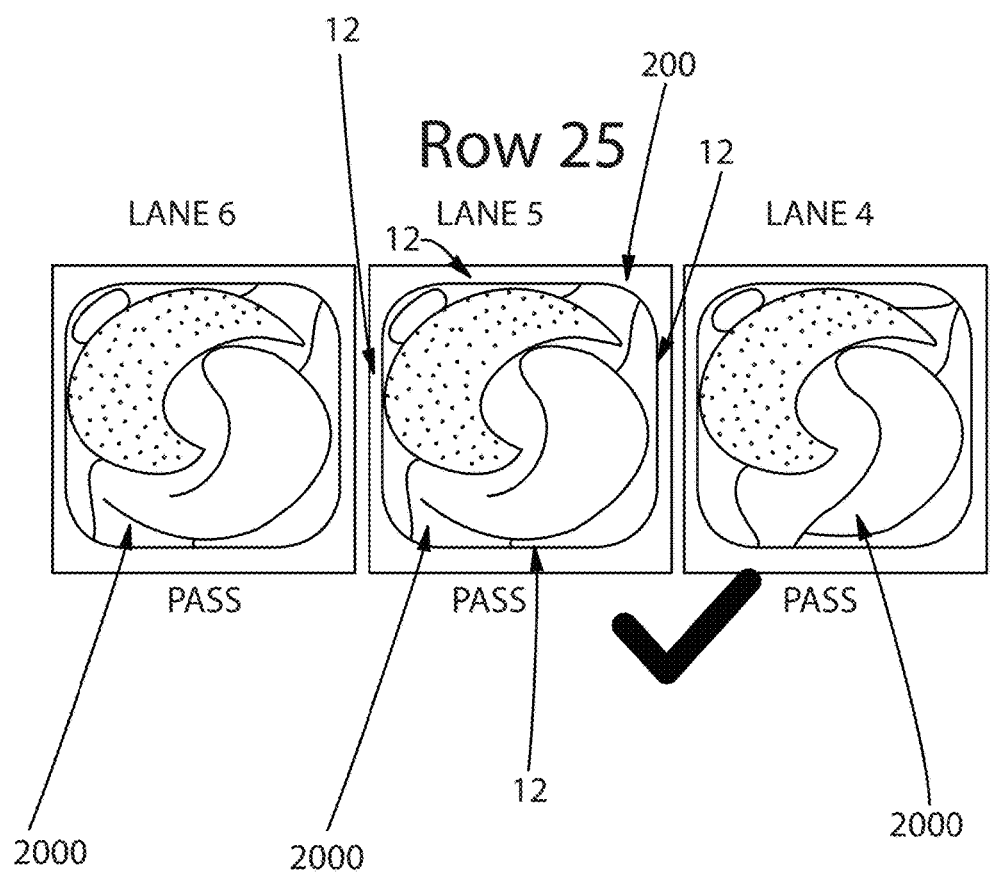
FIG. 5 is a picture of a row of pouches that have passed inspection.

FIG. 5 shows an image captured by one of the four cameras. In this embodiment, the camera is precisely aligned across the platen in the cross machine direction to line up with three pouches 2000 located in the pouch cavities and platen edges 12 adjacent to the cavities; the cavities themselves are not visible in FIG. 5 due to the presence of the pouches 2000 in the cavities. In this embodiment, the camera has reference regions shown as the light blue box 200 in alignment with the sides of the actual outer boundaries of the platen edges 12 surrounding each cavity.

In FIG. 5, no actinic radiation is detected on any of the platen edges 12, thus no leak is detected. The camera communicates a "pass" status for this row of pouches over an Ethernet IP protocol to the PAC.

Figure 6:
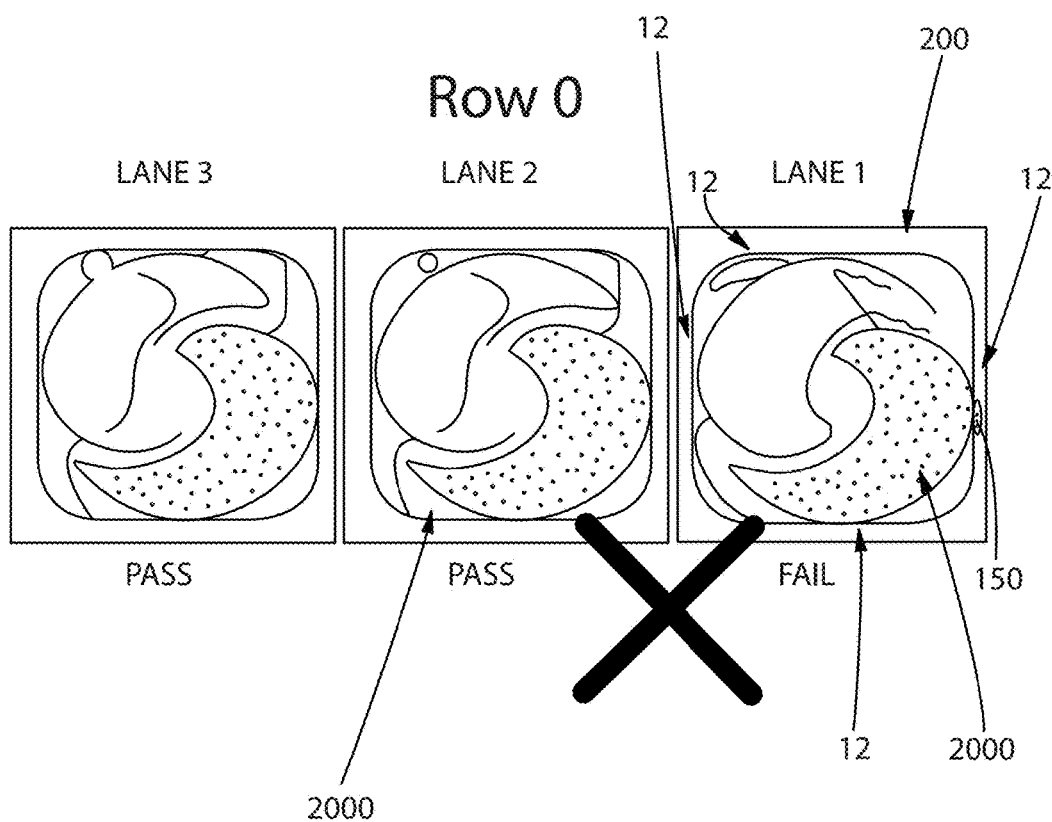
FIG. 6 is a picture of a row of pouches that have failed inspection.

FIG. 6 shows a row of pouches 2000 and associated platen edges 12. Actinic radiation 150 is detected on the platen edge 12 to the right of the pouch 2000 on the far right. Thus a leak is detected on the right platen edge 12 of this pouch. The camera communicates a "fail" status of this row over the Ethernet IP protocol to the PAC. The PAC then directs that leaky pouch and its neighbor to be ejected from the converting line.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A converter-integrated machine vision method for detecting leakage from a composition-containing pouch, wherein:
   a) the pouch is located in a cavity of a platen, the platen being disposed in a pouch converting line, the platen comprising a plurality of mold cavities;
   b) the composition is selected from the group consisting of: light duty liquid detergent compositions, heavy duty liquid detergent compositions, granular detergent compositions, hard surface cleaning compositions, detergent gels, bleach and laundry additives, shampoos, body washes and combinations thereof; and wherein the composition comprises a photosensitive compound responsive to actinic radiation, wherein the photosensitive compound is selected from the group consisting of: fluorescent dyes, ultraviolet dyes, near infrared dyes, infrared dyes and combinations thereof; and
   c) the platen has a plurality of platen edges adjacent to the cavity;

the method comprising the steps of:
   i. exposing at least one of the plurality of platen edges to an actinic radiation-emitting source;
   ii. obtaining, with an imaging unit, an image of the at least one of the plurality of platen edges exposed to the actinic radiation-emitting source;
   iii. detecting, with an imaging processing unit, actinic radiation emission if present on the at least one of the plurality of platen edges; and
   iv. sending a fail message to a controller if the actinic radiation emission is detected, wherein when the controller detects actinic radiation emission at at least one platen edge, the controller then directs that the pouch in the cavity adjacent the at least one platen edge be ejected from the converting line.

2. The method according to claim 1, wherein the actinic radiation-emitting source is selected from the group consisting of: an ultraviolet light; a white light; a near infra red light; an infra red light; and combinations thereof.

3. The method according to claim 1, wherein the photosensitive compound is selected from the group of: C.I. Fluorescent Brightener 260, C.I. Fluorescent Brightener 351, 2,2'-(1,2-ethenediyl)bis[5-[[4,6-bis(phenylamino)-1,3, 5-triazin-2-yl]amino]benzenesulfonic acid, the compound having the following structure:

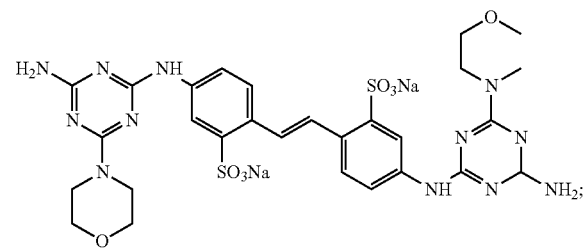

and
   mixtures thereof.

4. The method according to claim 3, wherein the photosensitive compound is present in the composition at from about 50 parts per million ("ppm") to about 2500 ppm.

5. The method of claim 4, wherein the photosensitive compound is present in the composition at from about 100 ppm to about 2000 ppm.

6. The method of claim 1, wherein the controller is selected from the group consisting of: a programmable logic controller and a programmable automation controller.

7. The method of claim 6, wherein the controller is a programmable automation controller.

8. The method according to claim 1, further comprising the step of moving the platen with continuous movement in a machine direction.

9. The method according to claim 1, wherein the mold cavities are located on the curved surface of a drum.

10. The method according to claim 1, wherein the plurality of cavities comprises mold cavities in a machine direction and mold cavities in a cross machine direction, and wherein a line scan camera is part of a plurality of cameras that are positioned above the platen and span the platen in a cross machine direction.

11. The method according to claim 1, wherein when the controller directs that the pouch in the cavity adjacent the at least one platen edge where actinic radiation emission is detected be ejected, the controller further directs that the neighboring pouch also be ejected from the converting line.

12. A converter-integrated machine vision method for detecting leakage from a composition-containing pouch, wherein:
   a) the pouch is located in a cavity of a platen, the platen being disposed in a pouch converting line, the platen comprising a plurality of mold cavities, wherein the plurality of cavities comprises mold cavities in a machine direction and mold cavities in a cross machine direction;
   b) the composition is selected from the group consisting of: light duty liquid detergent compositions, heavy duty liquid detergent compositions, granular detergent compositions, hard surface cleaning compositions, detergent gels, bleach and laundry additives, shampoos, body washes and combinations thereof; and wherein the composition comprises a photosensitive compound responsive to actinic radiation; and
   c) the platen has a plurality of platen edges adjacent to the cavity;
the method comprising the steps of:
   i. exposing at least one of the plurality of platen edges to an actinic radiation-emitting source;
   ii. obtaining, with an imaging unit, an image of the at least one of the plurality of platen edges exposed to the actinic radiation-emitting source, wherein the imaging unit comprises a line scan camera that is part of a plurality of cameras that are positioned above the platen and span the platen in a cross machine direction;
   iii. detecting, with an imaging processing unit, actinic radiation emission if present on the at least one of the plurality of platen edges; and
   iv. sending a fail message to a controller if the actinic radiation emission is detected, wherein when the controller detects actinic radiation emission at at least one platen edge, the controller then directs that the pouch in the cavity adjacent the at least one platen edge be ejected from the converting line.

13. The method according to claim 12, wherein the photosensitive compound is selected from the group consisting of: fluorescent dyes, ultraviolet dyes, near infrared dyes, infrared dyes and combinations thereof.

14. The method according to claim 12, wherein the actinic radiation-emitting source is selected from the group consisting of: an ultraviolet light; a white light; a near infra red light; an infra red light; and combinations thereof.

15. The method according to claim 12, wherein the photosensitive compound is selected from the group of: C.I. Fluorescent Brightener 260, C.I. Fluorescent Brightener 351, 2,2'-(1,2-ethenediyl)bis[5-[[4,6-bis(phenylamino)-1,3,5-triazin-2-yl]amino]benzenesulfonic acid, the compound having the following structure:

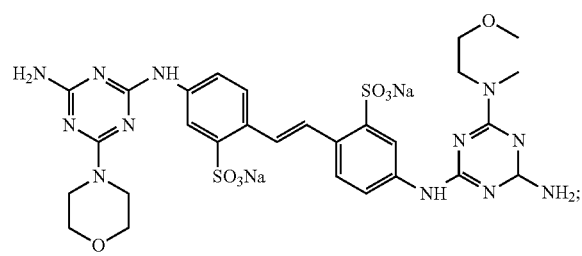

and
   mixtures thereof.

16. The method according to claim 12, wherein the photosensitive compound is present in the composition at from about 50 parts per million ("ppm") to about 2500 ppm.

17. The method of claim 16, wherein the photosensitive compound is present in the composition at from about 100 ppm to about 2000 ppm.

18. The method of claim 12, wherein the controller is selected from the group consisting of: a programmable logic controller and a programmable automation controller.

19. The method of claim 18, wherein the controller is a programmable automation controller.

20. The method according to claim 12, further comprising the step of moving the platen with continuous movement in a machine direction.

21. The method according to claim 12, wherein the mold cavities are located on the curved surface of a drum.

22. The method according to claim 12, wherein when the controller directs that the pouch in the cavity adjacent the at least one platen edge where actinic radiation emission is detected be ejected, the controller further directs that the neighboring pouch also be ejected from the converting line.

* * * * *